United States Patent [19]

Ohmura et al.

[11] 4,424,206

[45] Jan. 3, 1984

[54] PROCESS FOR HEAT TREATMENT OF AQUEOUS SOLUTION CONTAINING COLD INSOLUBLE GLOBULIN TO INACTIVATE HEPATITIS VIRUS

[75] Inventors: Takao Ohmura, Takarazuka; Yutaka Hirao, Toyonaka; Satoshi Funakoshi, Katano, all of Japan

[73] Assignee: The Green Cross Corporation, Osaka, Japan

[21] Appl. No.: 351,299

[22] Filed: Feb. 22, 1982

[30] Foreign Application Priority Data

Feb. 25, 1981 [JP] Japan .................................. 56-27448

[51] Int. Cl.³ ...................... A61K 35/14; A61K 37/00
[52] U.S. Cl. .................................. 424/101; 424/177; 260/112 B
[58] Field of Search ............................. 424/101, 177; 260/112 B

[56] References Cited

U.S. PATENT DOCUMENTS 4,305,871 12/1981 Shanbrom ..................... 260/112 B
4,327,086 4/1982 Fukushima et al. ................ 424/101

OTHER PUBLICATIONS

Shikata et al.–J. of Infect. Dis., vol. 138, No. 2 (Aug. 1978), p. 242.

*Primary Examiner*—Sam Rosen
*Attorney, Agent, or Firm*—Cushman, Darby & Cushman

[57] ABSTRACT

Cold insoluble globulin which may have hepatitis virus activity can be virus-inactivated with keeping at a minimum the damage of the cold insoluble globulin by heating its aqueous solution at 50° to 80° C. for 5 to 20 hours in the presence of 10% (W/V) or more of at least one principal stabilizer of neutral amino acids, monosaccharides, disaccharides, and sugar alcohols with or without 10% (W/V) or more of at least one auxiliary stabilizer of salts of hydrocarbon carboxylic acids or hydroxyhydrocarbon carboxylic acids both having 3 to 10 carbon atoms.

17 Claims, No Drawings

PROCESS FOR HEAT TREATMENT OF AQUEOUS SOLUTION CONTAINING COLD INSOLUBLE GLOBULIN TO INACTIVATE HEPATITIS VIRUS

This invention relates to a process for heat treatment of an aqueous solution containing a cold insoluble globulin.

A cold insoluble globulin (hereinafter referred to as CIG) has hitherto been called "large eternal trypsin sensitive protein (LETS)", "cell surface protein (CSP)", "cell adhesion factor (CAF)" or "opsonic $\alpha_2$ surface binding glycoprotein (O-$\alpha_2$SBG)" and so forth, but recently it is generally called CIG or fibronectin. It is a glycoprotein having a molecular weight of 440,000 which occurs in, besides plasma, mesenchymal cells such as fibroblast or basilar membrane such as epidermis. With regard to the other physicochemical properties known about CIG, there may be mentioned that the mobility is that of $\alpha_2$ globulin, the isoelectric point is 5.0, the molecular extinction coefficient $A_{1\,cm}^{1\%}$ 280 nm is 12.9–13.0, $S_{20,w}$ is 11–14S and the carbohydrate content is 5%.

In the coagulation of blood, the bonding between $\gamma$-chains of fibrin is accelerated by the transglutaminase action of the blood coagulation factor XIII, and the crosslinkage of fibrin is formed. In this instance the crosslinkage between $\gamma$-chains of fibrin is formed through CIG by the catalytic action of the same XIII factor, and the blood coagulation becomes more complete thereby CIG has also the function of effecting the adhesion or bonding between cells and cell sustentacular tissue and hence has the pharmacological efficacy to promote the wound healing of a trauma. The pharmacological efficacies thus far reported include the treatment for septic shock, and the treatment for infective diseases on the basis of its enhancing the opsonic action of a phagocyte. Moreover, it is known that CIG has the anticancer and antileukemia activity due to its action of enhancing intercellular adhesive property and of causing necrosis of a cancer cell. Accordingly a vast expectation is being placed on the chemical effect of CIG as a medicine.

Now then, CIG is obtained by separating from fibroblast, culture fluids thereof, fractions of plasma protein and so forth, and, when separated from these there is the danger of being contaminated with a virus and the like. Especially, when CIG is obtained from the fractionation of plasma protein the contamination with the hepatitis virus is apprehended, and is becoming one of serious problems. With regard to hepatitis B in particular, although much contribution has been made to the prevention of hepatitis B infection caused by plasma fraction preparations by subjecting to fractionation only the plasma which proved to be negative to the virus (hepatitis B virus: HBV) after examining the plasma material by use of a test method of high detecting sensitivity such as radioimmunoassy or reversed passive passive hemagglutination test, the perfect prevention is a remote possibility. That is to say, even when the hepatitis B surface antiger (HBsAg) is negative in the test by the above methods, there is still the possibility of $10^8$ of HBsAg present in 1 ml of the plasma, and this figure corresponds to $10^5$ as HBV.

In the plasma fractionation preparations which had the undeniable danger of causing the outbreak of hepatitis, the first success was achieved in inactivating the hepatitis virus by the heat treatment at 60° C. for 10 hours for alubumin preparations. It has been verified recently that the infectivity of the hepatitis virus can be diminished to 1/10,000 by this treatment.

In the case of CIG preparations for clinical applications also, it is very important that said preparations have been subjected to the heat treatment at 60° C. for 10 hours in order to prevent the hepatitis infection. But when the heat treatment is carried out in conventional aqueous solutions such as a physiological saline solution, the greater part of the CIG loses its activity or the protein molecules thereof undergo denaturation.

The present inventors, after intensive studies, found out that, when an aqueous solution containing CIG was subjected to a heat treatment for the purpose of inactivating the hepatitis virus, the heat stability of CIG to the heat treatment was markedly increased by adding a neutral amino acid, a monosaccharide, a disaccharide and/or a sugar alcohol (these are hereinafter referred to generically as a principal stabilizer), and also found out that the heat stability of CIG was further increased by the further coexistence of, in addition to the above principal stabilizers, a specified salt of an organic carboxylic acid (hereinafter referred to simply as an auxiliary stabilizer). The present invention has been accomplished on the basis of these findings.

Thus, the present invention relates to a process for heat treatment to inactivate the hepatitis virus of an aqueous solution containing a cold insoluble globulin, which comprises carrying out the heat treatment of the aqueous solution containing the cold insoluble globulin in the presence of at least one principal stabilizer selected from the group consisting of neutral amino acids, monosaccharides, disaccharides and sugar alcohols.

The present invention further relates to the above process for heat treatment, which comprises carrying out the heat treatment in the presence of, in addition to the above principal stabilizer, at least one auxiliary stabilizer selected from organic carboxylic acid salts having 3–10 carbon atoms, which may have a hydroxy group.

As the aqueous solutions cotaining CIG of the present invention, there ma be used in general an aqueous solution containing CIG originated from a plasma protein fraction, fibroblast or a culture liquid thereof. The aqueous solution containing CIG to be used may be in any stage of purification ranging from unpurified to purified aqueous solution. But advantageously an aqueous solution in a partly purified or a purified stage is subjected to the heat treatment, and the protein (including CIG) concentration thereof is preferably 0.1–10% W/V.

The symbol "% W/V" means herein a percentage of a solute by weight per a solution by volume.

The pH of the said aqueous solution is generally 5–10, and is favorably adjusted to 6.5–8.5 with a buffer solution of a low salt concentration.

The principal stabilizers to be used according to the present invention include, for example, glycine, ananine, valine, leucine and isoleucine as neutral amino acids (i.e. monoamino monocarboxylic acids); glucose, mannose, galactose and fructose as monosaccharides; sucrose, maltose and lactose as disaccharides; and mannitol, sorbitol and xylitol as sugar alcohols; but they are not limited to the above examples. The amount to be added of the said principal stabilizer is 10–50% W/V, and 10–30% W/V in practice.

The organic carboxylic acid having 3–10 carbon atoms used auxiliarily as the stabilizer according to the present invention is referred to a hydrocarbon substituted with a carboxyl group, and the hydrocarbon radical therein may be either saturated or unsaturated. Examples of such hydrocarbon radicals include, for example, an alkyl, an aryl (e.g. phenyl) and an aralkyl group, which may have a hydroxyl group. The number of carboxyl groups in said organic carboxylic acid may singular or plural, preferably one or two. Said organic carboxylic acid may also be substituted by a hydroxyl group. Though the salt of said organic carboxylic acid is not specifically restricted so long as it is physiologically acceptable, an alkali metal salt (e.g. sodium salt and potassium salt) and an alkaline earth metal salt (e.g. calcium salt) are preferred, and a sodium salt and a potassium salt are especially preferable.

Preferred examples of the said organic carboxylic acid salts are physiologically acceptable salts, in particular alkali metal salts (sodium salts and potassium salts), of propanoic acid, butanoic acid, pentanoic acid, caprylic acid, caproic acid, malonic acid, succinic acid, glutaric acid, adipic acid, citric acid and mandelic acid.

The amount of the organic carboxylic acid to be added is 10–30% W/V, and 10–20% W/V in practice.

The heat treatment is carried out at a temperature and for a period of time which are sufficient to inactivate the hepatitis virus but to retain the activity of CIG, for example, for about 5–20 hours, preferably for about 10 hours at about 50°–70° C., preferably at about 60° C.

The stabilizer remaining in the aqueous solution after the heat treatment for inactivating the hepatitis virus can be removed by dialysis, especially by dialysis under reduced pressure accompanied by concentrating, or as the supernatant from the precipitation treatment with ammonium sulfate.

This invention will be illustrated in more detail with reference to the following examples, but it is not limited thereto.

REFERENCE EXAMPLE

Pooled human blood plasma from normal adults is fractionated with ethanol, and from the fraction I thus obtained CIG is purified by a suitable method. For example, according to the method of Matsuda et al (Ann. N.Y. Acad. Sci., 312, 74, 1978), the fraction I is dissolved in a 0.055 M sodium citrate buffer solution, pH 6.0, and 0.01 M of EACA ($\epsilon$-aminocaproic acid) and 10 units/ml of Aprotinin (trypsin inhibitor) are added to the solution to prevent the decomposition of CIG caused by plasmin. After plasmin and plasminogen have been removed by use of lysine-Sepharose prepared by coupling lysine to Sepharose ® (Cross-linked agarose, sold by Pharmacia, Sweeden) activated with cryanogen bromide, 10 units/ml of heparin is added, and the solution is kept at 0°–2° C. for 48 hours, and the precipitate is collected.

The precipitate is washed with each of a 0.05 M phosphate buffer solution, pH 6.0, and a 0.05 M citrate buffer solution which contains 1 M glycine and 6.5% ethanol to remove soluble protein, and thereafter a 0.055 M citrate buffer solution, pH 6.35, is added and the whole is brought to room temperature to dissolve the precipitate. An analogous procedure of keeping at 0°–2° C. and of separating and washing the precipitate is repeated three times, and a cryofibrinogen braction containing CIG is obtained as the last precipitate.

The cryofibrinogen (precipitate) is dissolved in twice as much 0.05 M tris-phosphate buffer solution, pH 7.0, by weight as the raw material fraction I which was used to collect the cryofibrinogen, and is adsorbed on DEAE-Sephadex ® (cross-linked dextran bound diethylaminoethyl group, sold by Pharmacia, Sweden) equilibrated with a 0.05 M tris-phosphate buffer solution, pH 7.0, and, after the contaminating protein has been removed by washing with the same buffer solution and with a 0.09 M tris-phosphate buffer solution, pH 7.0, the CIG is eluted with a 0.2 M tris-phosphate buffer solution, pH 7.0.

EXAMPLE 1

To 1 l of an aqueous solution containing 30 mg/ml of CIG dissolved in a 0.05 M tris-phosphate buffer solution (pH 8.0) was added 1 Kg of sucrose. After being stirred thoroughly the mixture was heated at 60° C. for 10 hours. After cooling, the mixture was dialyzed against a 0.9% sodium chloride solution and then centrifuged. A clear solution was obtained.

Quantitative determination of CIG was made on the CIG thus obtained, according to a single radial immunodiffusion method, and showed that the recovery of CIG was 83%.

EXAMPLE 2

To 1 l of an aqueous solution containing CIG employed in Example 1 were added 1 Kg of sucrose and 190 g of sodium citrate. After being stirred throughly the mixture was heated at 60° C. for 10 hours. After cooling, the mixture was dialyzed against a 0.9% sodium chloride solution and then centrifuged. A clear solution was obtained.

Quantitative determination of CIG was made on the CIG thus obtained, according to a single radial immunodiffusion method, and showed that the recovery of CIG is 100%.

EXPERIMENTAL EXAMPLE 1

Each of the heat treated CIG's obtained in Example 1 and 2 was subjected to gel filtration by use of Sephadex G-200 with a 0.05 M tris-phosphate buffer solution, pH 7.0, and the fractions containing CIG were collected and saturated 40% with ammonium sulfate. The precipitates formed were collected and dialyzed against a 0.05 M tris-phosphate buffer solution (pH 7.0). A purified CIG solution of 1% protein concentration was obtained.

Immuno-electrophoresis was carried out on this solution by use of antihuman whole serum (rabbit). No precipitin line other than that of CIG was observed.

EXPERIMENTAL EXAMPLE 2

The purified CIG obtained in Experimental Example 1 was employed to immunize a rabbit, and antihuman CIG (heat treated) antiserum (anti-CIG $\textcircled{h}$) was thus obtained. Separately, CIG which had been purified according to a conventional method without a heat treatment was employed to immunize a rabbit, and antiserum (anti-Cig $\textcircled{n}$) was obtained. Micro-Ouchterlong technique was carried out by using both of above antiserum. The result revealed that the two kinds of purified CIG antigen with and without a heat treatment, when tested against anti-CIG $\textcircled{h}$ as well as anti CIG $\textcircled{n}$, gave precipitin lines which fused into one another completely and did not shown any spur or partial spur.

This showed that no denaturation was observed which would cause excess or deficiency of antigenicity to heat treated CIG.

EXPERIMENTAL EXAMPLE 3

An experiment was performed for the purpose of ascertaining the stabilizing effect according to the present invention. In this experiment, various kinds of stabilizers indicated in Table 1 and 2 were added in diverse amounts to 1 l of the same aqueous solution as employed in Example 1 containing 30 mg/ml of CIG, and the solution was heated at 60° C. for 10 hours. The percentage survival of total CIG value based on that prior to the heat treatment was shown in Table 1 and Table 2.

The results reveal that the heat stability of CIG is increased by the addition of various kinds of stabilizers (Table 1), and that the heat stability of CIG is further increased by the addition of the auxiliary stabilizer to the principal stabilizer (Table 2).

TABLE 1

| Principal Stabilizers | Concentrations (W/V %) | CIG survival Rates (%) |
|---|---|---|
| Glycine | 10 | 35 |
|  | 15 | 62 |
|  | 20 | 70 |
| Mannitol | 10 | 28 |
|  | 15 | 46 |
|  | 20 | 60 |
| Glucose | 10 | 16 |
|  | 30 | 38 |
|  | 50 | 51 |
| Sucrose | 10 | 43 |
|  | 30 | 75 |
|  | 50 | 83 |
| None |  | 0 |

TABLE 2

| Principal stabilizers and concentrations (W/V %) | Auxiliary stabilizers | Concentration (W/V %) | CIG Survival rates (%) |
|---|---|---|---|
| Sucrose 50 | Sodium citrate | 0 | 83 |
|  |  | 10 | 88 |
|  |  | 15 | 92 |
|  |  | 20 | 100 |
|  | Sodium caprylate | 0 | 83 |
|  |  | 10 | 90 |
|  |  | 15 | 93 |
|  |  | 20 | 98 |
| Glycine 20 | Sodium citrate | 0 | 70 |
|  |  | 10 | 75 |
|  |  | 15 | 77 |
|  |  | 20 | 88 |
|  | Sodium mandelate | 0 | 70 |
|  |  | 10 | 78 |
|  |  | 15 | 74 |
|  |  | 20 | 83 |
| None | None |  | 0 |

What is claimed is:

1. A process for heat treatment to inactivate the hepatitis virus in a cold insoluble globuline, which comprises carrying out the heat treatment at 50° to 80° C. of an aqueous solution containing the cold insoluble globulin for a time sufficient to inactivate the hepatitis virus but to retain the activity of the cold insoluble globulin said aqueous solution also containing 10% W/V or more of at least one stabilizer selected from the group consisting of neutral amino acids, monosaccharides, disaccharides, and sugar alcohols.

2. The process according to claim 1, wherein the heat treatment is carried out in the additional presence of 10% W/V or more of at least one another stabilizer selected from the group consisting of salts of hydrocarbon carboxylic acids and hydroxyhydrocarbon carboxylic acids, which have 3 to 10 carbon atoms.

3. The process according to claim 1 or 2, wherein the neutral amino acid is present and is glycine, alanine, valine, leucine or isoleucine.

4. The process according to claim 1 or 2, wherein the monosaccharide is present and is glucose, mannose, galactose or fructose.

5. The process according to claim 1 or 2, wherein the disaccharide is present and is sucrose, maltose or lactose.

6. The process according to claim 1 or 2, wherein the sugar alcohol is present and is mannitol, sorbitol or xylitol.

7. The process according to claim 1 or 2, wherein the stabilizer is present in an amount of 10-50% W/V.

8. The process according to claim 7, wherein the amount is 10-30% W/V.

9. The process according to claim 1 or 2, wherein the heat treatment is carried out for 5 to 20 hours.

10. The process according to claim 1 or 2, wherein the aqueous solution contains the cold insoluble globulin in a concentration of 0.1 to 10% W/V.

11. The process according to claim 1 or 2, wherein the heat treatment is carried out at a pH of 5-10 of the aqueous solution which has been made into a buffer solution.

12. The process according to claim 2, wherein the hydrocarbon carboxylic acid is propanoic acid, butanoic acid, pentanoic acid, caprylic acid, caproic acid, malonic acid, succinic acid, glutaric acid or adipic acid.

13. The process according to claim 2, wherein the hydroxyhydrocarbon carboxylic acid is citric acid or mandelic acid.

14. The process according to claim 2, wherein the salt is a sodium or potassium salt.

15. The process according to claim 2, wherein the another stabilizer is present in an amount of 10-30% W/V.

16. The process according to claim 1 or 2 wherein the heat treatment is carried out for about 10 hours at about 50°-70° C.

17. The process according to claim 1 or 2 wherein the heat treatment is carried out for about 10 hours at about 60° C.

* * * * *